United States Patent [19]
Levy et al.

[11] Patent Number: 5,882,328
[45] Date of Patent: Mar. 16, 1999

[54] METHOD TO PREVENT TRANSPLANT REJECTION

[75] Inventors: Julia G. Levy; Modestus O. K. Obochi, both of Vancouver, Canada

[73] Assignee: QLT Phototherapeutics, Inc., Vancouver, Canada

[21] Appl. No.: 759,318

[22] Filed: Dec. 2, 1996

Related U.S. Application Data

[63] Continuation-in-part of Ser. No. 371,707, Jan. 13, 1995, abandoned.

[51] Int. Cl.$^6$ .............................. A61N 1/30; I61M 31/00
[52] U.S. Cl. .............................. 604/20; 604/49; 424/810; 128/898
[58] Field of Search ................................. 604/19, 20, 48, 604/49; 514/885; 530/388.7, 388.73, 388.75, 388.8, 388.85; 424/810, 140.1; 128/898

[56] References Cited

U.S. PATENT DOCUMENTS

| | | |
|---|---|---|
| 4,294,824 | 10/1981 | Jones et al. . |
| 4,649,151 | 3/1987 | Dougherty et al. . |
| 4,683,295 | 7/1987 | Carson ..................................... 530/391 |
| 4,696,286 | 9/1987 | Cochrum . |
| 4,866,168 | 9/1989 | Dougherty et al. . |
| 4,883,790 | 11/1989 | Levy et al. . |
| 4,889,129 | 12/1989 | Dougherty et al. . |
| 4,920,143 | 4/1990 | Levy et al. . |
| 4,932,934 | 6/1990 | Dougherty et al. . |
| 4,946,438 | 8/1990 | Reemtsma et al. . |
| 4,961,920 | 10/1990 | Ward et al. . |
| 4,996,193 | 2/1991 | Hewitt et al. . |
| 5,002,962 | 3/1991 | Pandey et al. . |
| 5,028,594 | 7/1991 | Carson ..................................... 514/23 |
| 5,028,621 | 7/1991 | Dougherty et al. . |
| 5,064,952 | 11/1991 | Chang et al. . |
| 5,087,636 | 2/1992 | Jamieson et al. . |
| 5,095,030 | 3/1992 | Levy et al. . |
| 5,135,915 | 8/1992 | Czarniecki et al. . |
| 5,145,863 | 9/1992 | Dougherty et al. . |
| 5,147,289 | 9/1992 | Edelson . |
| 5,149,708 | 9/1992 | Dolphin et al. . |
| 5,171,741 | 12/1992 | Dougherty et al. . |
| 5,171,749 | 12/1992 | Levy et al. ............... 514/410 |
| 5,173,504 | 12/1992 | Dougherty et al. . |
| 5,192,312 | 3/1993 | Orton . |
| 5,214,036 | 5/1993 | Allison et al. . |
| 5,227,298 | 7/1993 | Weber et al. . |
| 5,238,940 | 8/1993 | Liu et al. ............... 514/410 |
| 5,244,914 | 9/1993 | Clauss et al. . |
| 5,283,255 | 2/1994 | Levy et al. . |
| 5,308,608 | 5/1994 | Dolphin et al. . |
| 5,314,905 | 5/1994 | Pandey et al. . |
| 5,368,841 | 11/1994 | Trauner et al. ............................. 424/9 |
| 5,545,423 | 8/1996 | Soon-Shiong et al. ................. 424/484 |
| 5,563,132 | 10/1996 | Bodaness ................................. 514/185 |

FOREIGN PATENT DOCUMENTS

| | | |
|---|---|---|
| 0 284 409 A2 | 9/1988 | European Pat. Off. . |
| WO 95/03814 | 2/1995 | WIPO . |
| WO 96/21466 | 7/1996 | WIPO . |
| WO 97/11653 | 4/1997 | WIPO . |

OTHER PUBLICATIONS

Obochi, M.O.K., et al., "Prolonged Skin Allograft Survival After Photodynamic Therapy Associated With Modification Of Donor Skin Antigenicity", *Transplantation* (1997) 63(6):810–817.
Waterfield, J.D., et al., "Evaluation of the Immunotoxicity of Benzoporphyrin Derivative (BPD–MA) in Mice," *Immunopharmacology and Immunotoxicology* (1997) 19(1):89–103.
Bowen et al., *Lancet* (1979) 2:585–86.
Faustman et al., *Proc. Natl. Acad. Sci. USA* (1981) 78:5156.
Gruner, S. et al., *Biomed. Biochim. Acta* (1986) 45(5):649–654.
Gruner, S. et al., *Scand J. Immunol.* (1985) 21:267–273.
Kocher, H.P. et al., *The Journal of Immunol.* (1979) 122(4):1190–1195.
Kohler, G. et al., *Nature* (1975) 256:495–497.
Kohler, G. et al., *European Journal of Immunol.* (1976) 6:511–519.
Lafferty et al., *Science* (1975) 188:259.
Lafferty et al., *Transplantation* (1976) 22:138–149.
Lau et al., *Science* (1984) 223:607.
Morgan, E.L. et al., *Scand J. Immunol.* (1979) 10:395–402.
Shizuri, A. et al., *Transplantation* (1986) 42:660.
Simkin, G. et al., *Proc. SPIE–Int. Soc. Opt. Eng.* (1995) 2392:23–33.
Spiegelberg, H.L. et al., *Immunoassays in the Clinical Laboratory* (1979) 1:1–22.

Primary Examiner—Wynn Wood Coggins
Assistant Examiner—Jennifer R. Sadula
Attorney, Agent, or Firm—Morrison & Foerster LLP

[57] ABSTRACT

Donor tissue containing antigen-presenting cells (APCs) can be modified to reduce rejection when the donor tissue is used as an allograft by exposing the donor tissue which has been treated with a photosensitizing agent having an absorption maximum between 400–900 nm to a wavelength absorbed by the photosensitizing agent so as to attenuate the APCs in the donor tissue but wherein the light is not cytotoxic to the APCs.

7 Claims, 5 Drawing Sheets

BPD-DA

BPD-DB

BPD-MA

BPD-MB

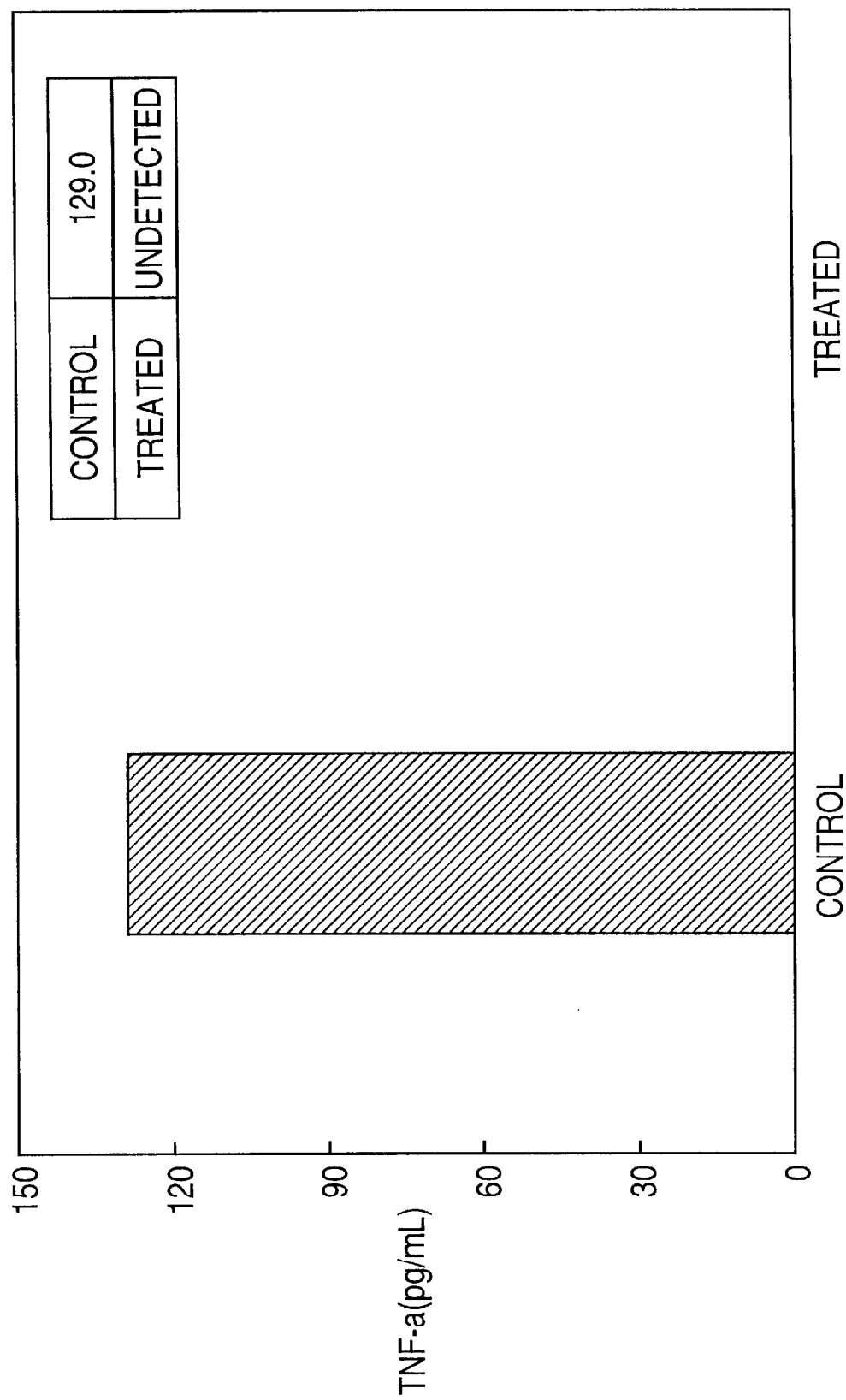

METHOD TO PREVENT TRANSPLANT REJECTION

This application is a continuation-in-part of U.S. Ser. No. 08/371,707 filed 13 Jan. 1995, and now abandoned.

TECHNICAL FIELD

The invention relates to procedures for supplying allografts in therapy and to preventing the rejection of allografts by a recipient. In particular, it concerns the treatment of donor tissue with photodynamic therapy techniques to (1) deplete or (2) to functionally attenuate rather than deplete, donor-derived antigen-presenting cells and to diminish the immunogenicity of other cells contained therein.

BACKGROUND ART

The success of a transplant of an allograft in a host depends on such factors as the antigens on the transplanted tissue that are recognized by the recipient as foreign and can evoke the rejection response, the cells in the recipient's immune system that mediate rejection, and the reactions that modify either the presentation of the foreign antigen or the cellular response. It is known that a significant component of allograft rejection is due to the presence in donor tissue of non-parenchymal cells (passenger leukocytes).

It is also known that the products of the major histocompatibility complex (MHC) play an important role in mediating an attack by the graft tissue against the recipient. The MHC is generally complex because it includes many different loci, each encoding separate cell-surface antigens, and because the loci have extensive polymorphism. The loci of the MHC fall into one of two classes, Class I or Class II, based on their tissue distribution, the structure of the expressed antigens, and their functions. Class I antigens, present on all nucleated cells, serve as the primary targets for cytotoxic T ($CD8^+$) lymphocytes. Class II antigens are not distributed in the tissue as widely and serve as primary targets for helper T ($CD8^+$) lymphocytes.

The polymorphic forms of the individual loci of human leukocyte antigen (HLA), the MHC in humans, have been recognized by antibodies and by various in vitro techniques that measure T-lymphocyte recognition. These responses, mediated by the recipients recognition of polymorphism in the donor, correlate with the strong rejection reactions that take place in vivo. Investigation into the cellular basis of graft rejection, using both in vitro and in vivo studies, has revealed that both $CD4^+$ and $CD8^+$ lymphocytes participate in the rejection response.

Attempts to prolong the survival of allografts and xenografts after transplantation, both in experimental models and in medical practice, have centered mainly on the suppression of the immune apparatus of the recipient. This treatment has as its aim preventive immunosuppression and/or treatment of graft rejection.

Examples of agents used for immunosuppression include cytotoxic drugs, antimetabolites, corticosteroids, and anti-lymphocytic serum. Nonspecific immunosuppressive agents found particularly effective in preventive immunosuppression (azathioprine, bromocryptine, methyl prednisolone, prednisone, and cyclosporin A) have significantly improved the clinical success of transplantation. The nephrotoxicity of cyclosporin A after renal transplantation has been reduced by co-administration of steroids such as prednisolone, or prednisolone in conjunction with azathioprine. In addition, kidneys have been grafted successfully using anti-lymphocyte globulin followed by cyclosporin A. Another protocol is total lymphoid irradiation of the recipient prior to transplantation, followed by minimal immunosuppression after transplantation. Treatment of rejection has involved the use of steroids, 2-amino-6-aryl-5-substituted pyrimidines, heterologous anti-lymphocyte globulin, and monoclonal antibodies to various leukocyte populations.

The principal complication of immunosuppressive drugs is infections. Additionally, systemic immunosuppression is accompanied by undesirable toxic effects, e.g., nephrotoxicity when cyclosporin A is used after renal transplantation, and reduction in the level of the hemopoietic stem cells. Immunosuppressive drugs may also lead to obesity, poor wound healing, steroid hypoglycemia, steroid psychosis, leukopenia, gastrointestinal bleeding, lymphoma and hypertension.

In view of these complications, transplantation immunologists have sought methods for suppressing immune responsiveness in an antigen-specific manner so that only the response to the donor alloantigen would be lost. Such specific immunosuppression generally has been achieved by modifying either the antigenicity of the tissue to be grafted or the specific cells capable of mediating rejection. In certain instances, whether immunity or tolerance will be induced depends on the manner in which the antigen is presented to the immune system.

Mason and Morris ("Effector Mechanisms in Allograft Rejection", Ann. Rev. Immunol. 4:119–45 (1986)) have suggested that a significant component of allograft rejection is the consequence of recipient T lymphocyte recognition of alloantigens expressed by immunostimulatory donor dendritic cells ("DC") present within the grafted tissue. It was logical, therefore, for anti-rejection strategies to focus on the modification and/or elimination of these MHC-bearing "passenger leukocytes" as a more selective and less toxic approach to prevent allograft rejection. It has been hypothesized that such treatment results in the depletion of passenger lymphoid cells and, thus, the absence of a stimulator cell population necessary to tissue immunogenicity.

Using a number of techniques, several attempts to diminish the antigenicity of donor tissues prior to transplantation have been made. The main focus of these attempts has been the total depletion of the donor-derived APCs. The effect of organ culture on the immunogenicity of MHC-incompatible allografts has been studied. Extended time culturing of the donor tissue (Lafferty et al., "Thyroid Allograft Immunogenicity Is Reduced after a Period in Organ Culture", Science, 188:259 (1975)) led to the prolongation of graft acceptance across MHC barriers. (Lafferty et al., *Transplantation*, 22:138–49 (1976); Bowen et al., *Lancet*, 2:585–86 (1979). Donor tissue has been treated with growth factor, such as TGF-beta (Czarniecki et al., U.S. Pat. No. 5,135,915 issued 4 Aug. 1992), sometimes in combination with extended culture times (Orton, U.S. Pat. No. 5,192,312 issued 9 Mar. 1993).

Furthermore, donor tissue has been treated with UV light Reemtsma et al., U.S. Pat. No. 4,946,438 issued 7 Aug. 1990; and Lau et al., "Prolongation of Rat Islet Allograft Survival by Direct Ultraviolet Irradiation of the Graft", *Science*, 223:607 (1984)). It has been suggested that UVB radiation may inhibit LC antigen-presenting cell function by preventing the expression of critical co-stimulatory molecules (Tang et al., *J. Immunol.*, 146: 3347 (1991); Simon et al., "Ultraviolet B Radiation Converts Langerhans Cells from Immunogenic to Tolerogenic Antigen-presenting Cells: Induction of Specific Clonal Anergy in CD4+ T Helper 1 Cells," *J. Immunol.*, 146:485 (1991)). Several authors have suggested that the exposure of LC to UVB or psoralen plus UVA radiation (PUVA) causes a loss of surface markers (including ATPase and class II MHC antigens) without causing overt cytotoxicity (Aberer et al., *J. Invest. Dermatol.* 76:202 (1981); Hanau et al, *J. Invest. Dermatol.* 85:135 (1985)). However, Tang and Udey (Tang et al, *J. Invest. Dermatol.*, 99:83 (1992)) showed that the levels of UV radiation that inhibited LC accessory cell function and selectively modulated ICAM-1 expression in short-term cultures were ultimately cytotoxic for LC.

Sometimes UV light has been used in conjunction with microencapsulation (Weber et al., U.S. Pat. No. 5,227,298, issued 13 Jul. 1993). Other workers have used barrier membranes alone, such as the bilayer comprising a first non-cytotoxic layer and a second outer layer of a biocompatible and semipermeable polymeric material taught by Cochrum, U.S. Pat. No. 4,696,286 issued 29 Sep. 1987.

Donor tissues has been treated with a wide variety of substances, such as the topical application of cyclosporin to skin grafts, as disclosed by Hewitt et al., U.S. Pat. No. 4,996,193 issued 26 Feb. 1991, and the perfusion of a donor kidney with lymphocytic chalone, as described by Jones et al., U.S. Pat. No. 4,294,824 issued 13 Oct. 1981. The survival time of skin grafts has been prolonged by treatment in vitro with cortisone, thalidomide, or urethane before implantation into a laboratory animal. The amount of drug locally applied to the skin is usually smaller than the amount required to achieve a similar effect by injecting the drug systemically into the recipient. Donor skin has been treated in vitro with streptokinase/streptodornase, RNA and DNA preparations of the recipient, or solutions of glutaraldehyde, prior to transplantation to reduce the antigenicity of the skin to be grafted.

More sophisticated approaches have involved the treatment of donor tissue with a monoclonal antibody directed against the MHC product along with complement (Faustman et al., "Prolongation of Murine Islet Allograft Survival by Pre-treatment of Islets with Antibody Directly to Ia Determinants", *Proc. Natl. Acad. Sci. USA*, 78:5156 (1981)) or the treatment of donor tissue with an immunoconjugate of antibody directed against the MHC (Shizuru, et al., "Inhibition of Rat Mixed Lymphocyte Pancreatic Islet Cultures with Anti-Ia Immunotoxin", *Transplantation*, 42:660 (1986)). Variable results were obtained by these methods.

However, based on the recent observation that microchimerism can exist for many years in the tissues of human solid organ allograft recipients (Starzl et al. "Chimerism and Donor-specific Nonreactivity 27 to 29 Years after Kidney Allotransplantation," *Transplantation*, 55:1272 (1993)), it has been hypothesized, albeit with much controversy, that microchimerism leads to a state of donor-specific tolerance. Starzl et al., "Liver Transplants Contribute to their Own Success", *Nature Med.*, 2:163 (1996). Since the migratory donor cells required to achieve microchimerism appeared to be the bone marrow-derived dendritic cells (Thomson et al., "Identification of Donor-derived Dendritic Cell Progenitors in Bone Marrow of Spontaneously Tolerant Liver Allograft Recipients", *Transplantation*, 60:1555 (1995)), it has been recognized that the total depletion of donor-derived DC may not be the best way to achieve the much desired donor-specific tolerance in cell, tissue or organ transplantation. For example, the findings of Rouabhia et al. (Rouabhia et al,. "Cultured Epithelium Allografts: Langerhans Cell and Thy-$1^+$ Dendritic Epidermal Cell Depletion Effects on Allograft Rejection", *Transplantation*, 56:259 (1993) suggested that the depletion of Langerhans cells (LC) might not be sufficient to sustain skin and epidermal sheet allograft survival.

The technique employed according the present invention for selectively depleting or attenuating these antigen presenting cells involves contacting donor tissue with a photosensitizer, followed by exposure to light, and then transplantation. Previously, photodynamic methods have-been used primarily for destroying tissues such as tumor tissues, atherosclerotic plaques, surface skin diseases, and unwanted pathogens in blood (Levy et al., U.S. Pat. Nos. 5,283,255 issued 1 Feb. 1994; 4,883,790 issued 28 Nov. 1989; 4,920,143 issued 24 Apr. 1990; 5,095,030 issued 10 Mar. 1992; and 5,171,749 issued 15 Dec. 1992, the disclosures of which are hereby incorporated by reference). See also, Dougherty et al., U.S. Pat. Nos. 4,932,934 issued 12 Jun. 1990; 4,889,129 issued 26 Dec. 1989; 5,028,621 issued 2 Jul. 1991; 4,866,168 issued 12 Sep. 1989; 5,145,863 issued 8 Sep. 1992; and 4,649,151 issued 10 Mar. 1987, which are also hereby incorporated by reference. The capacity of photosensitizers and light to destroy cancerous tissues and unwanted neovasculature constitutes the classical application of photodynamic therapy. Cell death results from either necrotic or apoptotic processes.

For example, U.S. Pat. No. 4,866,168 to Dougherty et al. discloses a composition sold under the trademark "Photofrin II", which is obtained by recovering the high aggregate-molecular weight portion of hematoporphyrin derivative. As another specific example, U.S. Pat. No. 4,883,790 to Levy et al. discloses the use of a group of related compounds designated "monohydrobenzoporphyrins" for analogous purposes.

In addition, the use of many various photosensitizers of similar structure has been described. See, for example, the derivatives of (1-hydroxyethyl)deuteroporphyrin, hydrophobic hematoporphyrin ethers, and compounds prepared from methyl pheophorbide (Pandey et al., U.S. Pat. No. 5,002,962 issued 26 Mar. 1991); pyropheophorbide conjugates (Pandey et al., U.S. Pat. No. 5,314,905); bacteriochlorophyll-a derivatives (Dougherty, U.S. Pat. Nos. 5,171,741 and 5,173,504); monovinyl and divinyl ether-linked dimers (Ward, U.S. Pat. No. 4,961,920); benzoporphyrin derivatives (Allison et al., U.S. Pat. No. 5,214,036); dibenzoporphyrin compounds Dolphin et al., U.S. Pat. Nos. 5,308,608 and 5,149,708); the so-called "green" porphyrins, such as monobenzoporphyrin derivatives (Jamieson et al., U.S. Pat. No. 5,087,636); porphyrin compounds containing exocyclic double bonds (Chang et al., U.S. Pat. No. 5,064,952); and porfimer sodium compositions (Clauss et al., U.S. Pat. No. 5,244,914). The disclosures of all of these patents are hereby incorporated by reference. In general, these drugs are regarded, in a first approximation, as being interchangeable in their utility with respect to photodynamic therapy.

While photodynamic therapy primarily concerns the treatment of tumor cells, additional applications have previously been shown. For example, these photosensitizing drugs can be used in protocols to eliminate atherosclerotic plaques, and in the treatment of blood and of other body fluids to destroy infectious organisms. Further, it has been shown that there is potential to use photodynamic therapy ("PDT") as an immunomodulatory technology for the treatment of a variety of autoimmune conditions. See Richter et al., "Activation of Benzoporphyrin Derivative in the Circulation of Mice without Skin Photosensitivity", *Photochem. Photobiol.* 59:3, 350–55 (1994); Chowdhary et al., "The Use of Transcutaneous Photodynamic Therapy in the Prevention of Adjuvant Enhanced Arthritis in MRL-1pr Mice", *Clin. Immunol. Immunopathol.* 72:2, 255–63 (1994); Hunt et al., "Transcutaneous Photodynamnic Therapy Delays the Onset of Paralysis in a Murine Multiple Sclerosis Model", *Proc.*

Soc. Photo-Optical Instr. Eng., 2371:451–55 (1994); and Obochi et al., "Targeting Activated Lymphocytes with Photodynamic Therapy: Susceptibility of Mitogen-stimulated Splenic Lymphocytes to Benzoporphyrin Derivative (BPD) Photosensitization", Photochem. Photobiol. 62:1, 169–75 (1995). It has been shown that exposure of freshly isolated murine Langerhans cells ("LC") to psoralen plus ultraviolet light A (UVA) radiation in vitro inhibited the accessory cell function of LC by decreasing their expression of the intracellular adhesion molecule-1 (ICAM-1). Tang et al., "Effects of Ultraviolet Radiation on Murine Epidermal Langerhans Cells: Doses of Ultraviolet Radiation that Modulate ICAM-1 (CD54) Expression and Inhibit Langerhans Cell Function Cause Delayed Cytotoxicity in vitro", J. Invest. Dermatol., 99:83–89 (1992).

While some workers in this field have shown that transdermal PDT profoundly suppressed contact hypersensitivity (CHS) and can enhance the length of skin allograft acceptance (Simkin et al., "Effect of Photodynamic Therapy Using Benzoporphyrin Derivative on Cutaneous immune Response", Proc. Soc. Photo-Optical Instr. Eng., 2392:23–32 (1995)), the specific cell targets have not been identified as yet for this kind of treatment. Possible candidates include activated lymphocytes in the circulation, activated macrophages or dendritic cells in the circulation, keratinocytes, and Langerhans cells ("LC") in the skin. It has now been found that the immunomodulatory effects of "low-dose PDT" of tissue grafts associated with extended engraftment may depend on a selective effect upon epidermal Langerhans cells ("LC") and may not require complete cell depletion, i.e., the eradication of passenger leukocytes, to permit acceptance of the allograft.

It is a particular advantage of the present invention that, unlike therapeutic regimens involving the administration of a photosensitizing drug to an organism, donor tissue may be most appropriately treated in vitro prior to an actual transplant procedure. In this manner, problems associated with ensuring proper levels of light exposure of, e.g., a conjugate associated with target cells within an organism, are substantially obviated.

Further, the method of the invention results in grafts that are immunologically stable in suitable hosts, biologically functional, and capable of being stored prior to transplantation. Thus, this invention enables the establishment of a bank of photodynamically treated grafts that can be used for short-term storage.

DISCLOSURE OF THE INVENTION

The invention provides a procedure for minimizing the rejection of transplants in animal subjects by modifying the antigenicity of donor tissue with low doses of photosensitizer and light ("low-dose" or "sub-lethal" PDT). Prior to transplantation, donor tissue, which contains antigen-presenting cells (APC's), is contacted with a photosensitizing agent and exposed to light having a wavelength absorbed by the photosensitizing agent for a time sufficient to deplete or attenuate the APC's. Moreover, "low-dose" or "sub-lethal" PDT does not necessarily cause cell death but still produces changes in certain cell populations that profoundly affect their expression of cell surface molecules and secretion of cytokines, thereby altering the functional attributes of the treated cells. This treatment does not kill epidermal cells but is thought to alter the expression of MHC (Class I and II antigens), and co-stimulatory (B7-1 and B7-2) molecules on Langerhans cells, as well as the cytokines secreted by epidermal cells (mainly keratinocytes and Langerhans cells), such that the immunogenicity of the skin itself is diminished.

In one embodiment, the photosensitizing agent is in the form of a conjugate comprising a target-specific component to enhance the interaction between the photosensitizing agent and the target APC's. The photosensitizing drug mediates the destruction of the APC's when the allograft is irradiated at a suitable wavelength absorbed by the photosensitizing agent.

In another embodiment, cells of the immune system and the skin may be sensitive to modulation by "sub-lethal" PDT. For example, changes at the molecular level in both lymphocytes and epidermal cells maybe caused by treatment with low levels of benzoporphyrin derivative monoacid ring A ("BPD-MA") and light. Treatment of skin with BPD and light at levels which significantly enhanced the length of murine skin allograft acceptance has been found to down-regulate the expression of Langerhans cell ("LC") surface antigen molecules, such as MHC and co-stimulatory molecules, and to regulate the formation of some cytokines, such as tumor necrosis factor-alpha (TNF-$\alpha$). In the invention, "sub-lethal" or "low-dose" PDT, using lower drug and light levels, significantly enhanced the length of skin allograft acceptance, as well as affecting surface antigen expression (MHC and co-stimulatory molecules) and accessory cell activity of epidermal Langerhans cells.

BRIEF DESCRIPTION OF THE DRAWINGS

FIG. 2 shows TNF-$\alpha$ levels in co-cultures of epidermal cells and T cells enriched via nylon wool adherence.

MODES OF CARRYING OUT THE INVENTION

Figure 1A:
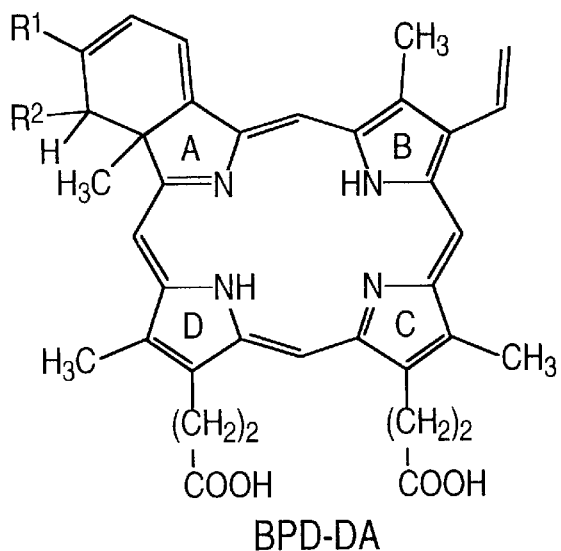
FIG. 1 shows the structure of BPD compounds particularly useful as photosensitizing agents in the invention.
Figure 1B:
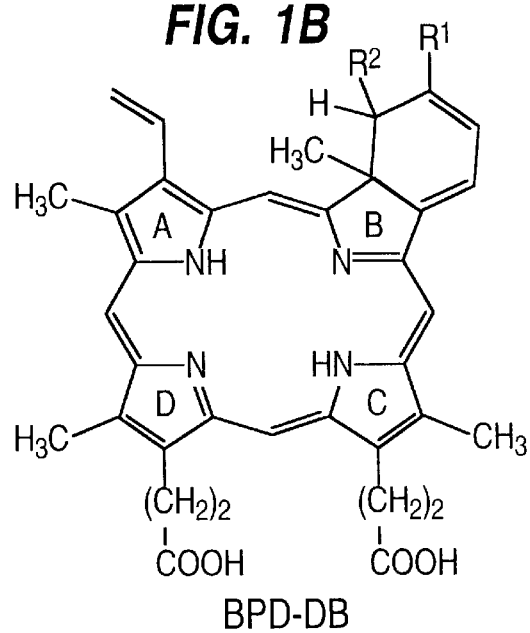
Figure 1C:
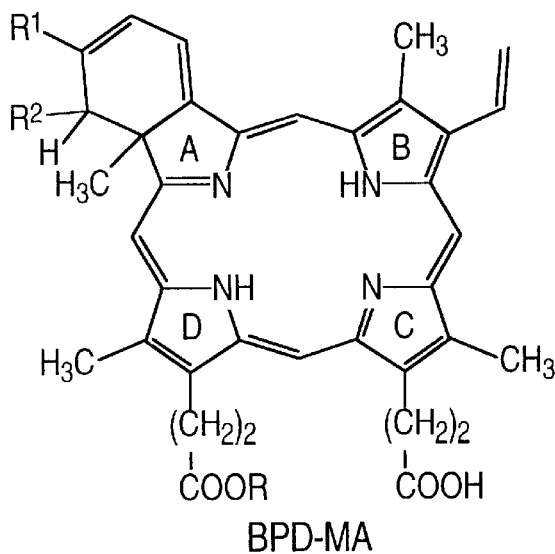
Figure 1D:
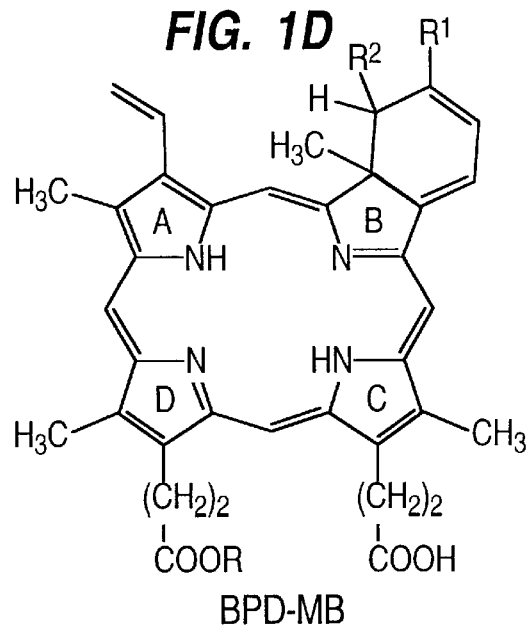

In accordance with the invention described below, prior to transplantation of donor tissue, it is contacted with a photosensitizing agent. The term "donor tissue" encompasses any types of transplantable or implantable tissue from a donor other than the recipient that contains APC's. The donor tissue being used in the invention may be any one of a wide variety of tissues, for example, soft tissue such as the amniotic membrane of a newborn, bone marrow, hematopoietic precursor cells, collagen, and bone protein to stimulate cartilage growth; organs such as skin, heart, liver, spleen, pancreas, thyroid lobe, lung, kidney, tubular organs (e.g., intestine, blood vessels, or esophagus); parts of organs, such as heart valves; and isolated cells or clusters of cells, such as islet cells of the pancreas or liver cells.

Tubular organs can be used to replace damaged portions of esophagus, blood vessels, or bile duct. Skin grafts can be used, not only for burns, but also as a dressing for a damaged intestine or to close certain defects such as a diaphragmatic hernia. In a particularly preferred embodiment, the donor tissue is skin tissue or pancreatic islet cells.

The term "graft" as used herein refers to biological material derived from a donor for transplantation into a recipient. The term "transplant" and variations thereof refers to the insertion of a graft into a recipient, whether the transplantation is syngeneic (where the donor and recipient are genetically identical), allogeneic (where the donor and recipient are of different genetic origins but of the same species), or xenogeneic (where the donor and recipient are from different species). Thus, in a typical scenario, the host is human and the graft is an isograft, derived from a human of the same or different genetic origins. In another scenario, the graft is derived from a species different from that into which it is transplanted, including animals from phylogenically widely separated species, for example, a baboon heart being transplanted into a human host.

The donor tissue can be taken from any source, whether from cadavers or living donors. Examples of suitable donors include live animals such as laboratory animals, for example, dogs, cats, mice, rats, gerbils, guinea pigs, cows, primates, or human beings. Donors are preferably mammalian, including human beings.

Human donors are preferably voluntary, blood-related donors that are normal on physical examination and of the same major ABO blood group, because crossing major blood group barriers can prejudice the survival of an allograft. It is, however, possible to transplant, for example, a kidney of a type O donor into an A, B or AB recipient.

The term "allograft" refers to cells and tissue that originate with or are derived from a donor of the same species as the recipient. Preferably, the donor is of the same species as the recipient.

The term "recipient" as used herein refers to any compatible transplant host. By "compatible" is meant a host that will accept the donated graft. Examples of potentially useful recipients includes animals, preferably mammals such as farm animals, for example, horses, cows or sheep; household pets, for example, dogs or cats; laboratory animals, such as mice, rats, gerbils or guinea pigs; or primates, for example, apes or human beings. Most preferably, the recipient is a human being. If both the donor of the graft and the host are human, they are preferably matched for HLA Class II antigens to as to improve histocompatibility.

Photosensitizing Agents

In general, any one of a great variety of compounds that are useful in classical photodynamic therapy are suitable for use in the present invention. As is well known to those of ordinary skill in this art, a major class of known photosensitizing agents are porphyrin-related compounds. As described in some detail above, these drugs include hematoporphyrin derivatives; the high molecular weight fraction of hematoporphyrin derivative, marketed as Photofrin II photosensitizing composition and the active components thereof; various synthetic derivatives of porphyrins, such as the monohydrobenzoporphyrins, also referred to as benzoporphyrinderivatives or BPD's; green porphyrins; and various other polycyclic compounds believed to generate singlet oxygen when irradiated, thus causing tissue destruction. Methods for the preparation of suitable photosensitizing compounds are fully disclosed in the patents described above, and in the publications cited therein. Preferably, the photosensitizing agent is BPD.

In principle, the critical feature of any photosensitizing agent is its propensity, when exposed with light of a wavelength capable of being absorbed by the photosensitizer, to exhibit a cytotoxic effect on cells in which it is localized. While it is believed that, in many instances, the cytotoxic effect is a result of the formation of singlet oxygen upon exposure, the exact mode of cytotoxicity, when it occurs, is not critical to the present invention.

As discussed at some length in the aforementioned Dougherty et al. patents, a number of additional specific properties are typically associated with effective photosensitizing agents. Among the properties of photosensitizers in general that are of particular significance in the practice of the present invention are a relative absence of toxicity to cells in the absence of the photochemical effect and a ready clearance from tissues in the absence of a target-specific interaction between particular cells and the photosensitizer.

The photosensitizing agents of the present invention preferably have an absorption spectrum which is within the range of wavelengths between 350 nm and 1200 nm, which absorption spectrum may be tailored to the desired penetration in a manner known per se, preferably between about 400 and 900 nm and, most preferably, between 600 and 800 nm.

The photosensitizing agents of the invention are dosed in a fashion consistent with good medical practice, taking into account the nature of transplantation and the disorder to be treated, the species of the donor, the medical condition of the individual recipient, the presence of any other drug in the donor tissue or in the recipient's body, and other factors known to practitioners. A therapeutically effective amount of photosensitizer used to contact the graft is an amount that is effective to reduce the immunogenicity of the graft so that it will be compatible with the recipient and not be rejected. A generally effective amount for this purpose is in the range of about 0.1 to about 10 $\mu$g/ml, preferably from about 0.1 to about 2.0 $\mu$g/ml and, most preferably, from about 0.25 to about 1.0 $\mu$g/ml.

The photosensitizing agent may be combined with one or more immunosuppressive agents to enhance the immunosuppressant effect on the graft. The effective amount of such other agents depends on the amount of the photosensitizing agent present in the formulation, the type of transplant, the cause of the transplant, the site of delivery, the method of administration, the scheduling of administration, other factors discussed above, and other factors known to practitioners.

Typically, the photosensitizing agent is formulated by mixing it, at ambient temperatures, appropriate pH's, and the desired degree of purity, with one or more physiologically acceptable carriers, i.e., carriers that are non-toxic to recipients at the dosages and concentrations employed. The pH of the formulation depends mainly on the particular use, and concentration of photosensitizer, but preferably ranges anywhere from about 3 to about 8.

Preferably, the photosensitizer is maintained at a neutral pH (e.g., about 6.5 to about 7.5) to prevent its adhering to the containers in which it is placed, as occurs at pH values approaching physiological levels, and to ensure activation of the photosensitizer. Thus, the formulation of a photosensitizer in an electrolyte solution containing a balanced salt buffer at pH 6.5, but containing no fetal bovine serum ("FBS"), is a suitable embodiment. The reason the FBS is omitted is because it contains antigenic components which could exacerbate the allograft reaction. If the photosensitizing agent adheres to the containers in which the grafts are being treated, an appropriate non-antigenic ingredient, such as human serum albumin, is optionally added in an amount that does not interfere with the photosensitizing agent perfusing or adhering to the graft being treated.

If the photosensitizing agent formulation is to be applied topically, for example, if it is to be painted onto a skin graft prior to transplantation, it is preferable to use a viscous solution such as a gel, rather than a non-viscous solution. The gel may be prepared, for example, by mixing a solution of the desired photosensitizing agent with a gelling agent, such as a polysaccharide, preferably a water-soluble polysaccharide, e.g., hyaluronic acid, starches, and cellulose derivatives (such as methylcellulose, hydroxyethyl cellulose, and carboxymethyl cellulose). When a polysaccharide is present in a gel formulation, the amount usually present is in the range of about 1–90% by weight of the gel, more preferably about 1–20%. Examples of other suitable polysaccharides for this purpose and a determination of the solubility of the polysaccharides are found in EP 267,015 published 11 May 1988, the disclosure of which is incorporated herein by reference.

If the graft to be treated is to be stored for any period of time, the photosensitizing agent is preferably formulated in or added to a perfluorochemical emulsion (acting as a blood substitute) to enable high concentrations of oxygen to reach the graft. Such emulsions comprise a perfluorochemical such as perfluorodecalin and/or perfluorotripropylamine emulsified with a surfactant in water. The perfluorochemical is chosen to be the least toxic to the recipient.

Examples of suitable surfactants include the poloxamer surfactants, which represent a series of molecules that are block copolymers of ethylene oxide and propylene oxide, either alone or taken in admixture with a phospholipid such as egg lecithin. Another example of an emulsion commercially available from Green Cross is Fluosol-DA 20%, which contains perfluorodecalin and perfluorotripropylamine emulsified with the poloxamer surfactant, Pluronic F-68. The perfluorochemical emulsions and their effects in mammals are described more fully in Bollands et al., *J. Pharm. Pharmacol.*, 39:1021–1024 (1987), the disclosure of which is incorporated herein by reference.

The photosensitizer formulation for use in therapeutic administration is preferably sterile. Sterility is readily accomplished by sterile filtration through 0.2 micron membranes. Once formulated and sterilized, the photosensitizer may not be stable to oxidative denaturation.

However, lyophilized formulations for reconstitution, for example, containing BPD, are suitable for storage.

Targeting Systems

The use of these photosensitizing agents in destroying the ability of donor tissue to initiate a graft-versus-host reaction is enhanced by conjugation of the photosensitizer to a target-specific agent. In particular, the photosensitizing material may be conjugated to (1) a moiety that specifically targets the antigen-presenting cells (APC's) in the donor tissue directly; (2) a moiety that specifically targets an intermediary material, which labels the APC's for targeting by the conjugate; or (3) T cells to a graft-vs.-host situation. In either case, once the donor tissue has been modified by interaction with the conjugate, it is exposed in a manner known per se so as to effect a substantial depletion or modification-of the pool of APC's in the donor tissue.

The invention provides specific, photosensitizer-containing conjugates useful to target APC's in allograft donor tissue, as well as a method to functionally attenuate or destroy APC's in donor tissue by photodynamic therapy ("PDT") generally. One formulation useful in this process consists essentially of a photosensitizing agent and a system for linking a "homing agent" with the photosensitizer. Another formulation comprises the combination of an APC-targeting system and a photosensitizing agent conjugated with a homing agent for the APC-targeting system. With either formulation, the ultimate objective of delivering the photosensitizing drug to the APC's is identical.

The targeted APC's can be accessed by a variety of different types of target-specific agents, including moieties immunospecific for the MHC glycoprotein products and lymphokine factors for which these cells bear receptors. Typically, for reaction with the MHC glycoproteins, antibodies raised against these glycoproteins, either polygonal or monoclonal, may be used.

Polyclonal antisera are prepared in conventional ways, for example by injecting a suitable mammal with antigen to which antibody is desired, assaying the antibody level in serum against the antigen, and preparing anti-sera when the titers are high. Monoclonal antibody preparations may also be prepared conventionally, such as by the methods of Koehler et al., "Continuous Cultures of Fused Cells Secreting Antibody of Predefined Specificity", *Nature (Lond.) (England)*, 256:5517, 495–97 (1975) or Koehler et al., "Derivation of Specific Antibody Producing Tissue Culture and Tumor Line by Cell Fusion", *Eur. J. Immunol (West Germany).*, 6:7, 511–19 (1976). These methods, for example, immortalize peripheral blood lymphocytes or spleen cells from immunized animals, by viral infection, fusion with myelomas, or other conventional procedures, and screen for the production of the desired antibodies by isolated colonies.

In addition to antibodies, suitable immunoreactive fragments may also be employed, such as the Fab, Fab', or F(ab)2 fragments. Many antibodies suitable for use in forming the targeting mechanism are already available in the art. For example, the use of immunologically reactive fragments as substitutes for whole antibodies is described by Morgan et al., "Comparison of the Binding of Radiolabeled Human IgG and Fc Fragments to Murine Spleen Cells", *Scand. J. Immunol. (Norway)*, 10:5, 359–402 (1979), and Kocher et al., "Tryptic Degradation of the C(H1) and V(L) Regions of IgD and IgE", *J. Immunol. (USA)*, 122:4, 1190–95 (1979).

In addition to immunoreactivity, targeting can be effected by using receptor ligands that target receptors at the APC cell surface, for example, on the basis of complementarity of contours or charge patterns between the receptor and ligand. As used herein, the term "receptor ligand" refers to any substance, natural or synthetic, that binds specifically to an APC cell surface receptor. These receptor ligands include lymphokine factors, for example, IL2.

In accordance with a particular embodiment of the present invention, the photosensitizing agent is conjugated with a target-specific agent for an intermediary which, in turn, is specific for the APC. For example, in the case of rat cells presenting Ia, mouse anti-rat Ia antibody could be used as an intermediary. In this case, a conjugate of photosensitizing agent coupled with anti-mouse antibody would target cells labeled with the murine antibody in precisely the same manner as a conjugate comprising anti-rat Ia antibody would do directly.

Conjugation Methods

The targeting system can be conjugated directly to the photosensitizing drug using conventional methods and linker technology, as are generally known in the art and described by way of example in the aforementioned Levy et al. patents. For proteins such as Ig and other polypeptides, a direct covalent bond may be effected between the photosensitizing agent and the target-specific component using, e.g., a dehydrating agent such as a carbodiimide. Active moieties of the conjugate may, of course, also be joined through the use of linker compounds that are bifunctional and capable of covalently binding with each of the two active components.

Any effective technique known in the art to be suitable for joining two chemical moieties falls within the scope of the invention. The linker moiety is to be broadly understood as being a covalent bond or any linker moiety available in the art or derivable therefrom using standard techniques.

Alternatively, the targeting can be mediated by additional specific agents. For example, as illustrated below, a secondary antibody directed to the APC-specific antibody may be linked directly to a photosensitizer, and the MHC-glycoprotein targeting agent may be used as a bridge between the immunoconjugate and the targeted cell.

Treatment Protocol

Elimination or functional attenuation of APC's, or modulation of other skin cells such as keratinocytes, in accordance with the present invention is effected in a relatively straightforward manner by contacting donor tissue directly with the photosensitizing agent, which may be in conjugate form, under conditions that enable the formation of a strong association between the photosensitizing agent (or the target-specific component of a photosensitizer-containing conjugate) and the target APC's, while minimizing the concentration of the photosensitizer in donor tissue.

The contact suitably involves applying the composition to one or more surfaces of the graft, or incubating or perfusing an organ graft, with the photosensitizer formulation of the invention. Contact with the photosensitizer generally takes place for at least one minute, preferably from about 1 minute to about 72 hours, and even more preferably from about 2 minutes to about 24 hours. The time of contact depends on such factors as the concentration of the photosensitizing agent in the formulation, the graft to be treated, and the particular type of formulation. Perfusion is accomplished by any suitable procedure. For example, an organ can be perfused via a device that provides a constant pressure or perfusion having a pressure regulator and overflow situation between a pump and the organ. Alternatively, the organ may be placed in a hyperbaric chamber via a sealing door, and perfusate delivered to the chamber by a pump that draws the fluid from a reservoir, optionally while spent perfusate is return to the reservoir by a valve.

For skin grafts, the formulation can be painted or sprayed onto the lower surface of the skin to be grafted, so that there is a layer of the photosensitizer between the lower surface of the donor and the tissue of the recipient. Preferably, however, the whole skin graft is submerged in the photosensitizer composition.

The contacting step can take place over a wide variety of temperatures, avoiding only those temperatures great enough to denature or otherwise deleteriously affect the graft and those temperatures low enough to minimize cellular uptake of the photosensitizer. Preferably, the contacting step takes place at a temperature in the range from about 5° C. to about 40° C., preferably, from about 15° C. to about 37° C. and, most preferably, at ambient temperature.

Following an appropriate distribution of the photosensitizer to ensure that it is properly associated with the target APC's, the thus-treated donor tissue is subjected to exposure with light having a wavelength that is absorbed by the photosensitizing agent and leads to activation of the photosensitizer's cytotoxic or immunomodulatory properties. Cytotoxic exposure is, of course, entirely conventional in the art of photodynamic therapy. Exemplary methods and apparatus for this purpose are described, for example, in the aforementioned Dougherty et al. patents.

After the graft has been contacted with photosensitizer and exposed to light, it can be stored for as long as about 24–48 hours. Preferably, however, it is used immediately in a transplant procedure. Storage life can be enhanced as described above by using a blood substitute in the formulation (e.g., a perfluorochemical emulsion), or by perfusing the graft with a formulation of the photosensitizing agent containing chilled isotonic agent and anticoagulant, followed by glycerol, to allow for the freezing of grafts with little destruction of the cells, as described in JP 60061501 published 9 Apr. 1985. In addition, the graft can be preserved with different liquids that include the photosensitizer formulation while the organs are being cooled to freezing temperatures, to preserve the organ semi-permanently without cell necrocytosis.

Before transplantation, the graft is preferably washed free of the photosensitizing agent composition, for example, by soaking it in a physiological saline solution or by other means appropriate for this purpose. Also, prior to transplantation, the recipient may be given one or more donor-specific blood transfusions with PDT-treated peripheral blood mononuclear cells to aid in graft survival. An alternative procedure is to subject the recipient to total lymphoid irradiation prior to the transplantation operation. Any other pre-transplant procedures that would be beneficial to the particular transplant recipient can be performed as part of the method of this invention.

In some instances, it is desirable to modify the surface of the graft so as to provide positively or negatively charged groups, as by using a suitable amino acid or polymer or by attaching a physiologically acceptable source of charged functional groups. For example, a negatively charged surface is appropriate for blood vessels to diminish blood clotting. It also is desirable in certain circumstances to render the surface hydrophobic or hydrophilic by coupling, e.g., phenylalanine, serine, or lysine, to the surface. An immunosuppressive agent particularly effective for these surface modifications is glutaraldehyde.

The transplantation procedure itself will depend on the particular disorder being treated, the condition of the patient, and the like. The medical practitioner will recognize the appropriate procedure to use in any given case. The transplants are optionally monitored systematically during the critical post-operative period (the first three months) using any suitable procedure, such as radionuclide intravenous angiography. After the transplantation, immunosuppression therapy, using an appropriate immunosuppressant, is often used as important in ensuring graft survival.

The method of the invention can be supplemented by or used in combination with the same or reduced dosages of immunosuppressive agent simultaneously administered to the donor systemically, the donor tissue in vitro, or the recipient, either locally or systemically. The term "immunosuppressive agent" as used herein refers to substances that act to suppress or mask the immune system of the host into which the graft is being transplanted. This would include substances that suppress cytokine production, downregulate or suppress self-antigen expression, or mask the MHC antigens.

Examples of such agents include 2-amino-6-aryl-5-substituted pyrimidines; azathioprine or cyclophosphamide; bromocryptine; glutaraldehyde; antiidiotypic antibodies for MHC antigens; cyclosporin A; one or more steroids, preferably corticosteroids and glucocorticosteroids such as prednisone, methyl prednisolone, and dexamethasone; anti-interferon-gamma antibodies; anti-tumor necrosis factor-alpha antibodies; anti-tumor necrosis factor-beta antibodies; anti-interleukin-2 antibodies; anticytokine receptor antibodies such as anti-IL-2 receptor antibodies; heterologous anti-lymphocyte globulin; pan-T antibodies, preferably OKT-3 monoclonal antibodies; antibodies to CD4; streptokinase; streptodomase; or RNA or DNA from the host.

An effective amount, which is determined by these considerations, is the minimum amount necessary to prevent an immune response that would result in rejection of the graft by the recipient, but as much as necessary to achieve a longer graft survival time. Such amount is preferably below the amount that is toxic to the recipient or renders the recipient significantly more susceptible to infections. The amount of immunosuppressive agent required for the invention is typically lower than that normally required for transplanted grafts that have not been pre-treated, and depends on the individual circumstances surrounding the transplant and the type of immunosuppressive agent being used.

As a specific example, the total pharmaceutically effective amount of the immunosuppressive agent, cyclosporin A, administered parenterally per dose will be in the range of about 0.1 to 20 mg/kg of patient body weight per day, as compared with the typical range of about 5 to about 15 mg/kg/day cyclosporin A currently used in conventional immunosuppressive therapy. For renal transplants, the usual practice is to administer massive doses of glucocorticosteroid at short periods, e.g., methylprednisolone in several-gram doses per day given for 3 to 5 days, followed by 20 to 100 mg prednisone, without photodynamic pre-treatment of the graft tissue. With the pre-treatment of the invention, significantly lower doses would be useful.

As noted above, these suggested amounts of immunosuppressant are subject to a great deal of therapeutic discretion. The key factor in selecting an appropriate dose and scheduling is the result obtained, i.e., graft survival long-term. For example, a relatively high dose may be needed either initially for the treatment of hyperacute graft rejection, which can be attributed to antibody-mediated graft destruction, or at a later stage characterized by a sudden decline in graft function.

When an immunosuppressive agent is used, it may be administered by any suitable means, including parenteral, and, if desired for local immunosuppressive treatment, intralesionally. Parenteral infusions include intramuscular, intravenous, intraarterial, intraperitoneal, and subcutaneous administration. In addition, when an immunosuppressive agent is used, it is suitably administered by pulse infusion, particularly with declining doses, or by continuous infusion.

The following examples are meant to illustrate, but not to limit, the invention:

EXAMPLE 1

Preparation of a BPD-Ra-MIg Conjugate

The photosensitizing agent, benzoporphyrin derivative monoacid ring A ("BPD-MA") shown in FIG. 1, is diluted, in the dark, from a concentration of 1 mg/ml to 200 pg/ml in phosphate-buffered saline and mixed with a known quantity of rat anti-mouse Ig (RaMIg), which is obtained from Cedar Lane Laboratories or prepared by immunizing rabbits with mouse immunoglobulin and purifying the antibodies over immunoabsorbent columns. The mixture is incubated at room temperature for one hour in the dark, and the resulting conjugate is dialyzed overnight through a membrane permeable to molecules having a molecular weight of less than 12–14 kd against three liters of PBS at 4° C. Model studies with labeled BPD-MA show that the retained conjugate has a BPD:Ab ratio of 10–20. The retentate from the dialysis is then frozen, lyophilized, and stored in the dark.

EXAMPLE 2

Treatment of Allograft Tissue with the Conjugate

Donor pancreatic islet tissue was isolated from rats as follows:

Male SD rats (200–250 g) were anaesthetized with intraperitoneal urethane (100 mg/kg) and, through a midline laparotomy, cardiorespiratory arrest was induced with bilateral pneumothoraces. The proximal common bile duct was cannulated and distally occluded at its point of entry into the duodenum. The pancreas was then distended in a retrograde fashion with cold (4° C.) collagenase solution (Type XI, Sigma Chemicals) at a concentration of 0.42 mg (650 U.) per ml. After in situ collagenase distention, a total pancreatectomy was performed.

The glands were digested for 22 minutes in a 37° C. water bath. The digested glands were dispersed by trituration through a sterile, siliconized pipette. The crude tissue slurry was passed through a 200 micron screen filter to remove undigested ducts, blood vessels and lymph nodes, and was then centrifuged through a discontinuous dextran gradient consisting of two monolayers, having specific gravities of 1.065 and 1.031 respectively. The less dense islet tissue was aspirated from the monolayer interface, washed, and further purified by hand picking under a dissecting microscope. Using this technique, 300–400 functionally and morphologically intact islets were harvested per pancreas.

The islets were cultured in vitro for one day in Ham's F-12 medium supplemented with 25% calf serum, 15 mM HEPES buffer and 1% strepfungizone. The cultured islets were initially incubated with a commercially available mouse anti-rat Ia monoclonal antibody (designated OX-6), obtainable from SeraLab at 0.2 mg/ml for hours at $_{13}$°C. OX-6 is immunospecific against Class II MHC product.

Portions of the OX-6-treated islets were incubated with, respectively, (1) Ra-MIg-BPD conjugate having a ratio of 6.5 BPD:1Ab; (2) the same conjugate at a ratio of 20 BPD:1Ab; (3) a conjugate of BPD with the irrelevant antibody GA-7sIgG at 6.5 BPD:1Ab; (4) BPD alone; and (5) medium alone at 20° C. for two hours in the dark. The incubation mixtures were then exposed to 10 Joules/cm$^2$ of light energy at a wavelength of 400–800 nm. The irradiated cultures were tested histologically and for APC depletion.

EXAMPLE 3

Characterization of Donor Tissue

In the histological studies, about 75–100 islets that had been treated with the conjugate of 6.5 BPD:1Ab were transplanted under the kidney capsule of recipient syngeneic SD rats and allogeneic WF rats. In both the syngeneic and allogeneic transplants, all recipients gave successful results. In particular, there was observed complete replacement of the graft with lymphocytic infiltrate in both syngeneic and allogeneic transplants and no identifiable endocrine tissue in either.

In the APC depletion studies, the islets were primarily immunostained with the OX-6 antibody. The thus-treated cells were subjected to a secondary staining with FITC-labeled goat anti-mouse Ig (Jackson Laboratories) and subjected to fluorescent microscopy. In preparations that had been treated with the conjugates, no identifiable MHC Class II Cells were seen. In the controls (conjugate with irrelevant antibody, BPD alone, and medium), however, the presence of these cells was detected by fluorescence microscopy, since the FITC-labeled secondary antibody labeled the APC and emitted green fluorescence.

EXAMPLE 4

Prevention of Skin Allograft Rejection

To establish a baseline representing minimal rejection, nine syngrafts (donor and recipient being the same animal)

were performed on BALB/c mice, in accordance with standard procedures (Billingham et al., "The Technique of Free Skin Grafting in Mammals", *J. Exp. Biol.*, 28:385–99 (1951)), as follows: The truncal skin of the mouse being grafted was shaved and depilated. The mouse was then anaesthetized by intraperitoneal injection of a mixture of 20 μl ketamine hydrochloride, 10 μl xylasine, and 70 μl PBS, following which a full thickness of skin (1 cm×1 cm) was obtained by careful dissection, leaving a suitable graft bed and taking care to keep the panniculus carnosus intact.

The autologous skin grafts were then re-applied to the grafting site and held with in place by applying a few about four drops of Vetbond tissue adhesive to the interface between the graft and graft bed. The graft was pressed down with petroleum jelly-coated gauze sponges, and the graft and sponges were held in place with Vetrap bandaging tape, which was wrapped around the body to form a "body cast."

The success rate for long-term syngrafts, i.e., over 120 days, was greater than 90%. Graft rejection was considered complete when there was at least 80% necrosis of the graft. Graft survival was expressed as a mean in terms of survival time in days±the standard deviation.

Allogeneic skin transplants between C57BL/6 (donors, H-$2^b$) and BALB/c (recipients, H-$2^d$) mice were also performed as controls, using the same procedures as described above except that each skin graft was taken from a donor mouse and applied to the graft bed of a different recipient mouse. Briefly, the truncal skin of donor mice was shaved and depilated, following which full skin grafts (1 cm×1 cm) were obtained. The recipient mice were shaved and then anaesthetized by intraperitoneal injection of a mixture of 20 μl ketamine hydrochloride, 10 μl xylasine, and 70 μl PBS. The graft bed of each recipient was prepared by careful dissection of the truncal skin (1 cm×1 cm), taking care to keep the panniculus carnosus intact. The grafts were applied to the allogeneic grafting site, and held with in place by applying Vetbond tissue adhesive, petroleum jelly-coated gauze sponges, and Vetrap bandaging tape, to form a "body cast." The mean survival time was 11.1 days (1.9 standard deviation).

In accordance with the method of the invention, the skin sample to be grafted on a recipient was first contacted in vitro with a 1.0 μg/ml solution of the photosensitizing agent BPD for one hour. The skin was then suspended in an electrolyte solution containing no fetal bovine serum ("FBS") for 30 minutes and exposed to the red light of light-emitting diodes ("LEDs") (10 J/cm$^2$ at 690 nm±10 nm). Following this light treatment, the exposed skin was transplanted to a recipient mouse as described above. The animal was monitored for rejection from day 8 following transplantation.

The results are shown graphically below in Table 1 as the mean plus the standard deviation of the mean. The mean survival time for the allografts increased to 18.5 days (2.1 standard deviation). Group means were compared by the Student's t-test.

TABLE 1

| Type of Graft | Number of Test Animals | Mean Survival Time (Standard Deviation) |
| --- | --- | --- |
| Syngraft | 9 | Indefinite |
| Allografts | 16 | 11.1 days (1.9) |

TABLE 1-continued

| Type of Graft | Number of Test Animals | Mean Survival Time (Standard Deviation) |
| --- | --- | --- |
| Allograft with pre-treatment of donor skin | 6 | 18.5 days (2.1) |

The results suggested that the immunomodulatory effect of photodynamic treatment on tissue to be grafted could result in a significantly extended engraftment survival time.

The experiment was repeated to again compare allografts performed on Balb/c recipient mice with allogeneic skin pre-treated ex vivo with the photosensitizing agent BPD, varying the concentration from 0.125–1.0 μg/mL, and light, with standard control allografts. For this experiment, allografts were considered rejected in most instances when necrotic patches were first observed within the grafted tissue, i.e., the onset of rejection. The result of the effectiveness of pre-treating graft tissue with low-doses of BPD, with or without light, on skin allograft survival is shown on Table 2. It was observed that neither (1) incubation of tissue grafts with BPD without light exposure or (2) pre-treatment of tissue grafts with light in the absence of BPD, had any significant effect on allograft survival. On the other hand, the survival of grafts on mice given pre-treated skin tissues prior to implantation were prolonged significantly (p<0.0001 by analysis of variants ("ANOVA")) depending upon the dose of BPD. Higher doses of BPD did not result in longer survival of the skin allografts. Rather, the most beneficial effects of the treatment were observed at lower doses of BPD (0.25–0.5 μg/mL) (Table 2), as opposed to 1.0 μg/mL, and light.

TABLE 2

Allograft survival in Balb/c recipient mice given allogeneic skin pre-treated in vitro with BPD (0.125, 0.25, 0.5 or 1.0 μg/mL) and light (10 J/cm$^2$; 690 ± 10 nm wavelength).

| Treatment Group | MST Days ± Stdev* | Percent Prolongation† |
| --- | --- | --- |
| Control | | |
| Untreated (n = 42) | 9.3 ± 2.2 | — |
| 10 J/cm$^2$ LED light only (n = 15) | 8.4 ± 2.1 | -9.7 |
| 1.0 μg/mL BPD only (n = 5) | 10.2 ± 0.4 | 9.7 |
| 0.25 μg/mL BPD only (n = 5) | 9.8 ± 0.4 | 5.4 |
| PDT of Donor Skin (μg/mL BPD + 10 J/cm$^2$ LED) | | |
| 1.0 μg/mL BPD (n = 5) | 11.2 ± 0.4 | 20.4 |
| 0.5 μg/mL BPD (n = 10) | 15.0 ± 1.4§ | 61.3 |
| 0.25 μg/mL BPD (n = 20) | 16.9 ± 1.7¶ | 82.9 |
| 0.125 μg/mL BPD (n = 10) | 14.2 ± 2.5§ | 52.7 |

*Mean Allograft Survival Time Days ± Standard Deviation. Allograft rejection was scored at the onset of necrosis within the grafted tissue.
† Percent prolongation of allograft was calculated relative to the untreated group.
n refers to the number of animals, is listed in parenthesis.
§ p <0.001, and ¶ p <0.0001 by Student's t-test relative to the untreated group.
p <0.0001 by ANOVA at alpha = 0.05.

Because it appeared that increasing the dose of the photosensitizing agent did not itself significantly lengthen the survival time of engraftment, it was postulated that the immunomodulatory effects of photodynamic treatment of tissue to be grafted may depend upon selective effects on the cell populations in the skin and may not necessarily be due to the known cytotoxic, cell depletion effect of photodynamic therapy.

EXAMPLE 5

Histological Examination of Skin to be Grafted

To examine the effects of treating skin grafts with photodynamic therapy under conditions that result in prolonged survival times, skin samples were obtained and treated as described above, except with a different range of photosensitizing agent concentrations, i.e., 0.25 or 0.50 µg/ml of BPD. Some tissues were incubated in electrolyte solution alone, without any photosensitizer being present, as control samples. All tissue samples were incubated over a 24-hour period, after which a representative number was exposed to light. When given, light exposure was with red light at an energy level of 10 J/cm².

All samples were then placed in formalin and subjected to histological examination. Tissues incubated in electrolyte solution alone (control samples) or in a solution of 0.50 µg/ml of BPD, without being light exposed, appeared to be normal. However, samples treated with either 0.25 or 0.50 µg/ml of BPD, followed by treatment with red light, exhibited the following minimal histological changes 25 hours post treatment: nuclear enlargement, perinuclear vacuolation, decrease in eosinophilia of epithelial cells, increase in cytoplasmic volume, and increased intercellular spaces between keratinocytes on the epithelial surface. Essentially all the cells in the treated skin remained viable at a level comparable to untreated skin. However, since the cells in the epidermis are made up of over 90% keratinocytes and constitute only about 3–5% Langerhans cells, it was possible that the treatment could have eliminated many LC and, due to their low numbers in the skin, this would not be apparent by routine histology. The fact that the lowest doses of BPD were most beneficial for engraftment, however, argued against selective cell killing as the mechanism. Therefore, it was postulated that, based on these histological findings, the photodynamic treatment of the invention resulted in a small degree of cellular damage, rather than widespread cell death. The mechanism for this unexpected, non-cytotoxic effect was not known.

EXAMPLE 6

Effect of "Low-dose" PDT on the LC-dependent Proliferation of Alloreactive T Cells.

Since Langerhans cells ("LC") are known to be responsible for the induction of the T cell response in the mixed epidermal cell-lymphocyte reaction (MECLR) (Stingl et al., *J Immunol.*, 121:2005 (1978)), the effect of low-dose PDT on the ability of the density gradient-enriched epidermal LC to induce the proliferation of alloreactive T cells was evaluated. When epidermal cells are mixed with allogeneic T cells, the LC in the population usually present alloantigens (Class I and II) to the T cells. The proliferative response of the T cells is an indication of the magnitude of antigen presentation. The primary MECLR was performed as described by Grabbe et al, *J. Invest. Dermatol.*, 102:67 (1994).

Figure 3:
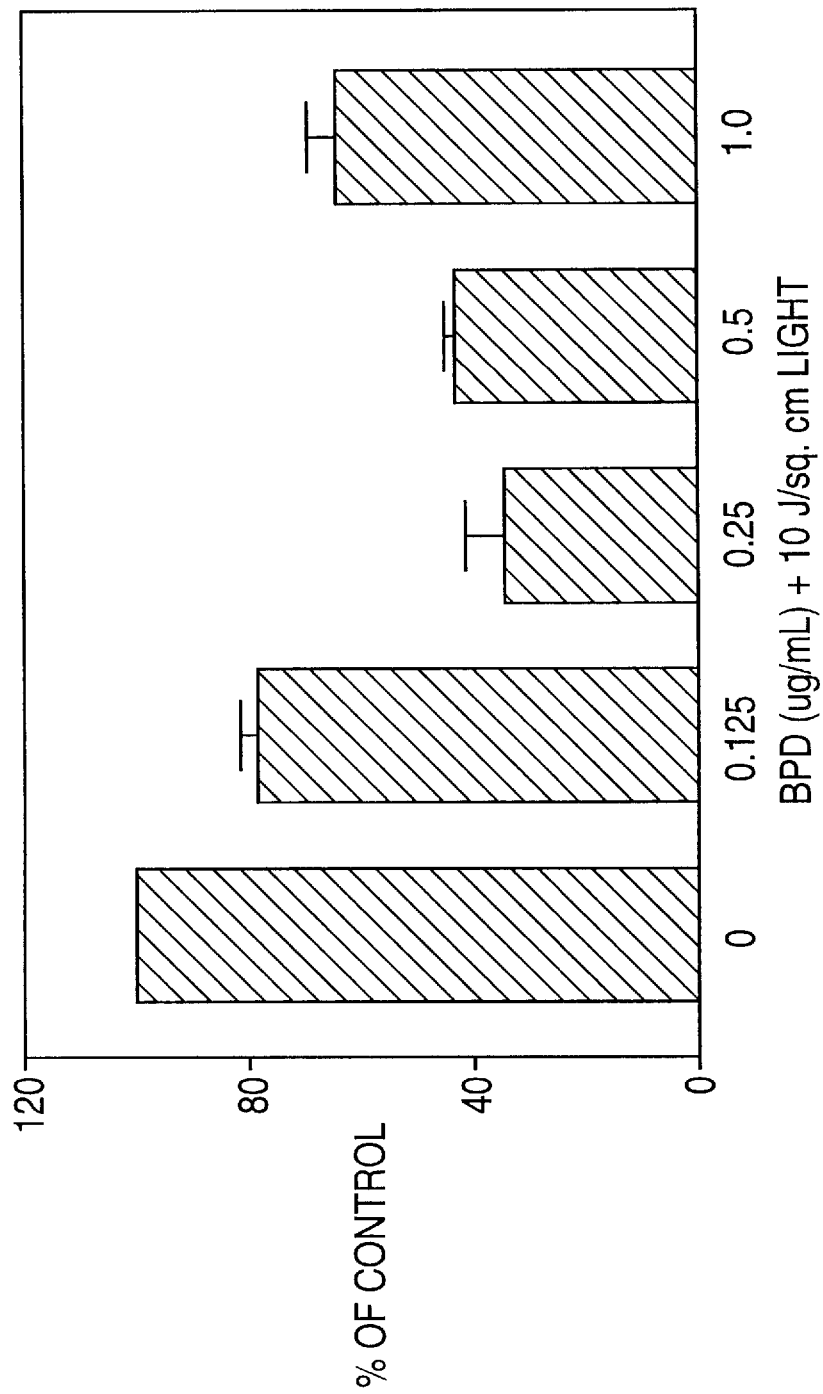
FIG. 3 shows the effect of "low-dose" PDT on the LC-dependent proliferation of alloreactive T cells.

Briefly, LC were enriched from treated (0–1.0 µg/mL BPD+10 J/cm² light) or untreated donor skin (C57BL/6) using a two-step density gradient centrifugation. Nylon-wool-enriched BALB/c cervical and inguinal lymph node T cells (4×10⁵ per well) were co-cultured with 1×10⁵ mitomycin C (Sigma)-treated (100 µg/mL at 37° C. for 20 minutes) C57BL/6 LC in complete culture medium. Cells were cultured in triplicates for 5 days at 37° C. in 96-well round-bottom microtitre plates (Falcon 3077, Becton Dickinson Labware, New Jersey). The resulting LC-dependent proliferation of allogeneic T cells in the MECLR, using LC from treated or untreated epidermis as stimulators, was quantified by non-radioactive MTT assay (Chen et al., "Colorimetric Assay Detects Mitogen Responses of Spleen But Not Blood Lymphocytes", *Int. Arch. Allergy Appl. Immunol.*, 93:249 (1990)). The results were expressed as mean percentages of control cells (treated with light only) taken as 100% response and are shown in FIG. 3 (n=3) ±SD. The results showed that low-dose PDT significantly (p<0.0001 by ANOVA) impaired the alloreactivity of LC. Optimal suppression of T cell proliferation in MECLR was obtained at 0.25 µg/mL of BPD when constant light was used, thus correlating with the optimal conditions for prolongation of skin allograft acceptance.

A microscopic observation of the cultures showed massive clusters of cells in the untreated controls, while there was limited clustering in the treated samples. The clusters of cells were thought to represent alloreactive T cells surrounding the LC. It has been shown that dendritic cells are the principal antigen-presenting cells that cluster with alloreactive T cells and are necessary for T cell proliferation in the mixed leukocyte response ("MLR").

Skin graft rejection, as well as the pathogenesis of a variety of cutaneous diseases, involves the production of cytokines by epidermal and inflammatory cells. Of great importance in the early phases of inflammatory reactions is a group of pleiotropic cytokines that includes interleukin ("IL")-1, IL-6, IL-8 and tumor necrosis factor-alpha ("TNF-α"). Accordingly, these pro-inflammatory cytokines have been found to be elevated during rejection episodes of allograft transplantation (Coito et al., "TNF-α Upregulates the Expression of Fibronectin in Acutely Rejecting Rat Cardiac Allografts", *Transplantation Proc.* 27:1, 463–65 (1995)). Thus, supernatants from the MECLR cultures above were obtained and also used to evaluate the effect of "sub-lethal" BPD and light on the secretion of TNF-α in the primary allogeneic response.

TNF-α was detected by a specific enzyme-linked immunosorbent assay ("ELISA") commercially available from Biosource International, California. The results are shown graphically in FIG. 2, which depicts the effect of "sub-lethal PDT" on TNF-α levels in co-cultures of epidermal cells and T cells enriched via nylon wool adherence in terms of pg/ml. The results suggested that pre-treatment of donor skin with transdermal PDT abrogated the secretion of TNF-α in an active immune response. Thus, when culture supernatants were measured for the presence of the immunostimulatory cytokine, TNF-α, it was found that significant levels were present in the control cultures, while none was detectable in the cultures containing PDT-treated epidermal cells. Since T cells are the major source of the TNF-α in MECLR, the drop in the levels of TNF-α production was thought to be a consequence of sub-optimal T cell activation.

These results show that one of the targets for transdermal PDT include LC which, as a result of the treatment, display impaired immunostimulatory properties. This mechanism possibly explains how photodynamic treatment prolongs skin allograft acceptance.

EXAMPLE 7

Effect of Low-dose PDT on the Immunocompetence of Pre-sensitized T cells.

Kripke et al., "Evidence that Cutaneous Antigen Presenting Cells Migrate Through Regional Lymph Nodes during Contact Sensitiziation", *J. Immunol.*, 145:2833 (1990) showed that epidermal LC migrate to the draining lymph nodes in response to the topical application of a contact allergen. Further, it has been implied that UV-altered LC may be responsible for the inducing anergy, as suggested by in vitro experiments using UV-irradiated LC (Simon et al., "Ultraviolet B Radiation Converts Langerhans Cells from Immunogenic to Tolerogenic Antigen-presenting Cells: Induction of Specific Clonal Anergy in CD4+ T Helper 1 Cells," J. Immunol., 146:485 (1991)). Therefore, we evaluated the immunocompetence of the T cells from the draining lymph nodes of graft recipients undergoing graft rejection.

Figure 4:
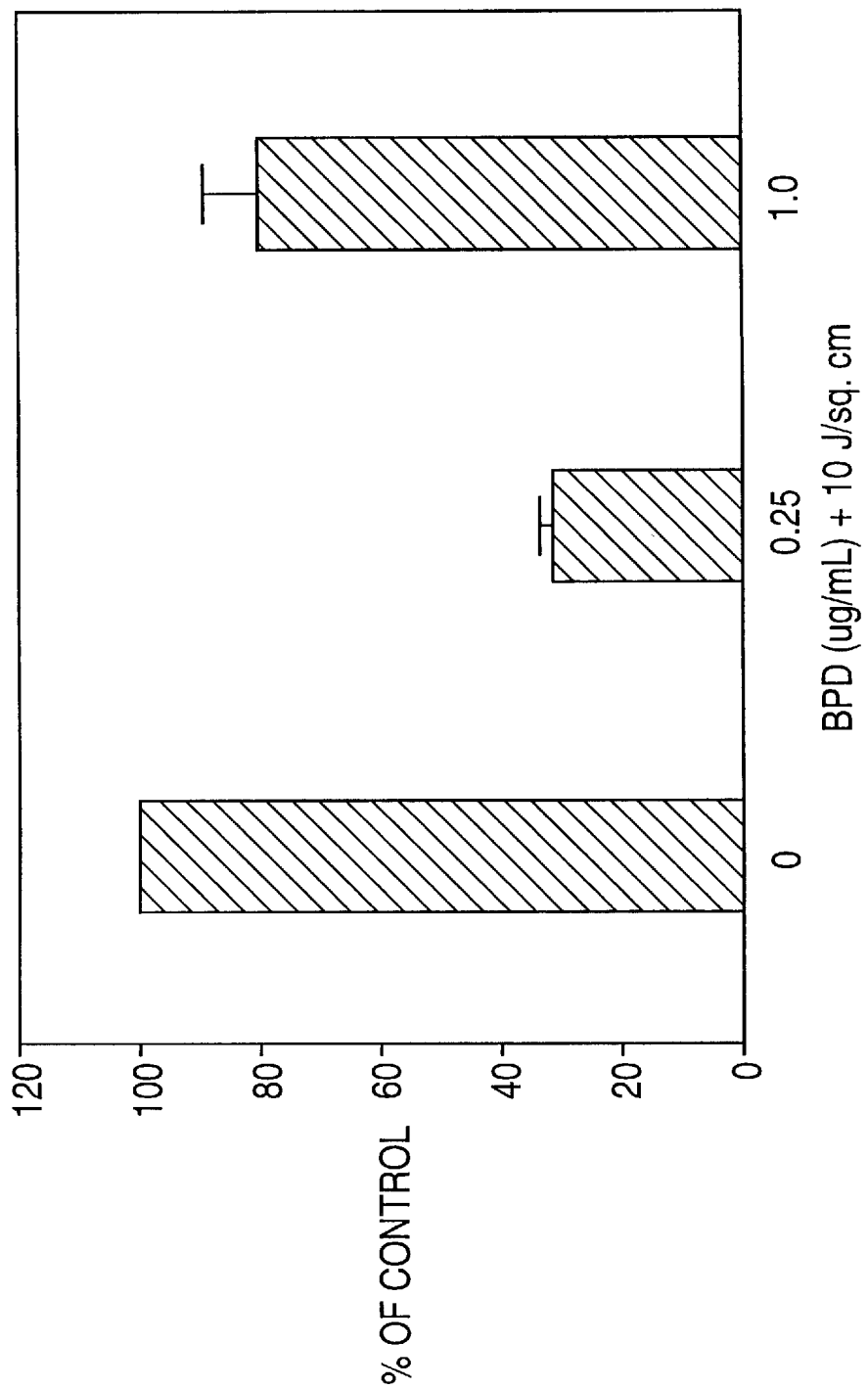
FIG. 4 shows the effect of low-dose PDT on the immunocompetence of pre-sensitized T cells.

Lymph node T cells from day-6 graft recipients were re-stimulated with freshly isolated untreated allogeneic LC (alloantigens) by co-culturing them in the MECLR as described above. The LC were enriched from untreated donor skin (C57BL/6) using a two-step density gradient centrifugation. Nylon wool-purified T cells ($4 \times 10^5$/well) and enriched LC ($1 \times 10^5$/well) were co-cultured in a humidified atmosphere for five days at 37° C. The proliferation of the primed T cells were quantified via the MTT assay and presented as a percent of control cells treated with light only and expressed as mean (n=3) ±SD. The results are shown in FIG. 4. The response of the primed, nylon wool-enriched T cells (procured from graft recipients given donor skins treated with low-dose PDT at BPD dose of 0.25 $\mu$g/mL) to re-stimulation with alloantigens was 30.5±1.9% in comparison with the untreated control group, taken as a 100% response. Similarly, the re-stimulation response of T cells from graft recipients transplanted with donor skins pre-treated with low-dose PDT at a higher BPD dose (1.0 $\mu$g/mL) was 79.5±8.5% relative to the control group.

EXAMPLE 8

Effect of "Low-dose PDT" on Langerhans Cell Surface Antigens.

Figure 5:
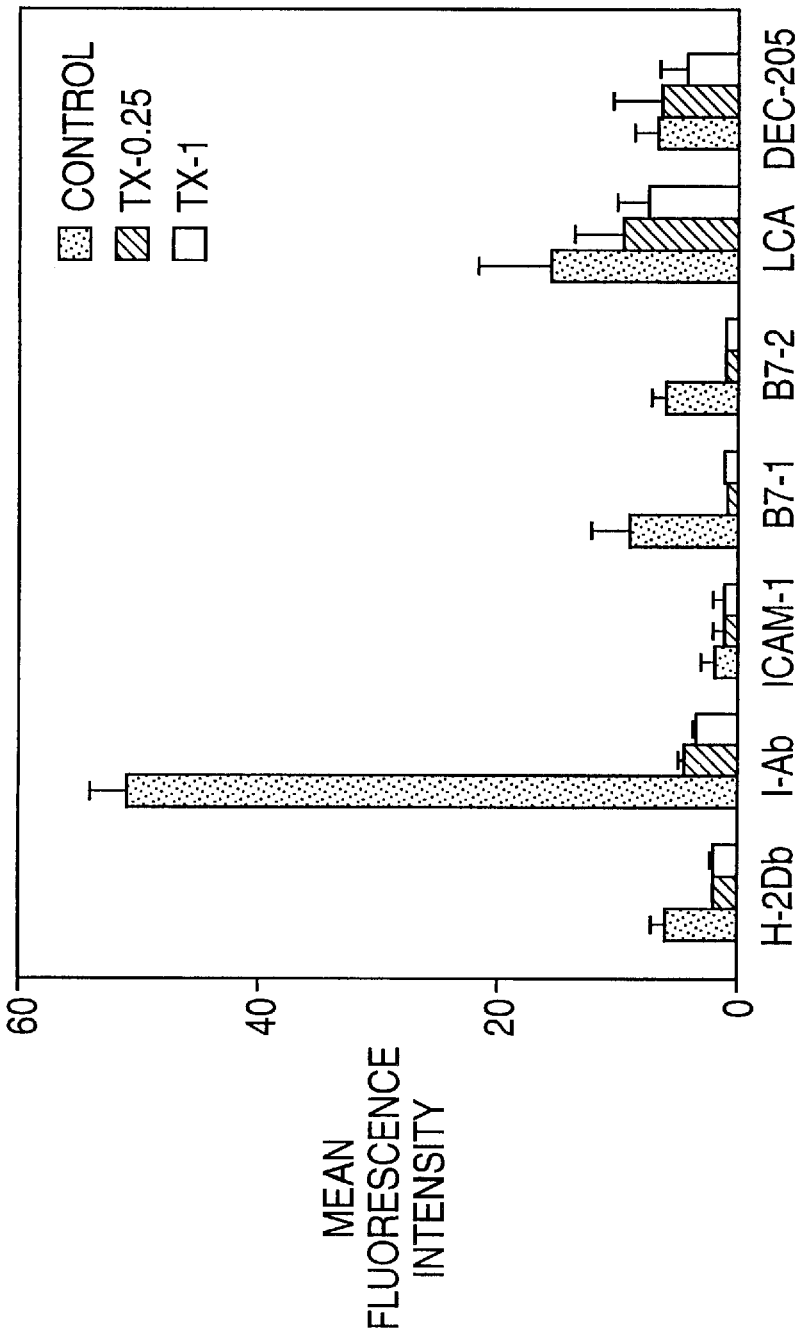
FIG. 5 shows the effect of low-dose PDT on Langerhans cell surface antigens.

The issue of whether the impaired alloreactive function observed in LC following low-dose PDT could also be explained by a decrease in the surface antigens on LC was also studied. Specifically, LC were enriched from treated (1.0 and 0.25 $\mu$g/mL BPD+10 J/cm$^2$ light) or untreated donor skin (C57BL/6) using a two-step density gradient centrifugation. Epidermal LC were stained with a panel of monoclonal antibodies and analyzed with an EPICS XL® flow cytometer. FIG. 5 shows the effect of "sub-lethal PDT" on the accessory cell activity of co-cultures of epidermal cells and T cells enriched via nylon wool adherence. The data shown represent the specific mean fluorescence intensities (intensity with the relevant monoclonal antibody minus the intensity with isotype-matched control IgG) expressed as mean (n=3) ±SD.

In this flow cytometric analysis of LC surface antigens, it was found that low-dose PDT at a BPD dose of 0.25 $\mu$g/mL and light, significantly ($p<0.001$ by ANOVA) decreased the LC surface molecules of MHC class I (H2$^b$) (62.8%), class II (I-A$^b$) (90.1%), B7-1 (89.2%), and B7-2 (80.0%), relative to the untreated groups. Data were expressed as mean proliferation fraction±SD (n=4) relative to untreated epidermal cells ($p<0.001$ by Student's t-test). Similar levels of reduction were obtained with low-dose PDT at a BPD dose of 1.0 $\mu$g/mL and light. However, the LC viability as well as the surface expression of CD45, ICAM-1 and DEC-205 were unaffected. This suggested that decreased levels of LC surface molecules after low-dose PDT was not likely to be the result of random events representing total collapse of the cell membrane or cytoskeletal structure of LC. Similar results have been reported elsewhere, e.g., with molecules (Tang et al.,*J. Immunol.*, 146: 3347 (1991)) using ultraviolet B (UVB).

In general, the enriched LC expressed distinct, albeit relatively low, ICAM-1, B7-1 and B7-2 molecules, but medium levels of class I and high levels of class II MHC molecules. This is in agreement with previous reports that LC freshly procured from mice are Ia$^{lo/hi}$/B7-1$^{-/lo}$/B7-2$^{-/lo}$, as opposed to cultured LC, which are known to express phenotype Ia$^{hi}$/B7-1$^{hi}$/B7-2$^{hi}$ (Xu et al., *J. Invest. Dermatol.*, 105:831 (1995); Inaba et al., *J. Exp. Med.*; 180:849 (1994)).

EXAMPLE 9

Effect of Low-dose PDT on Enriched LC in Short- and Long-term Cultures.

To exclude cytotoxicity of low-dose PDT for LC as a potential explanation for the decrease in cell surface antigens observed above, the effect of low-dose PDT on the in vitro survival of enriched murine LC was studied. Enriched LC were maintained in short-term (24-hour) or in long-term (7-day) cultures in complete culture medium supplemented with equal concentrations of granulocyte/macrophage-colony stimulating factor (GM-CSF) and macrophage-colony stimulating factor (M-CSF) (20 ng/mL; R & D Systems, Minneapolis, Minn.). GM-CSF and M-CSF have been shown to be optimal for LC survival in vitro (Xu et al., *Eur. J. Immuno.*, 25:1018 (1995); Kitajima et al., *J. Immunol.*, 155:5190 (1995). At the end of the incubation periods, cells were recovered, enumerated, and either assayed for viability or stained for MHC class II (I-A$^b$), B7-1, and B7-2 antigens. The resulting data are shown below in Table 3.

TABLE 3

Effect of low-dose PDT on LC, enriched from untreated or treated donor skin tissues, in short-term (24-hour) and long-term (7-day) cultures.

| GROUP | VIABILITY OF ENRICHED LANGERHANS CELLS$^a$ ± STANDARD DEVIATION (%) | | |
|---|---|---|---|
| | Fresh | Short-term culture | Long-term culture |
| Untreated Control | 79.6 ± 9.5 | 80.2 ± 4.0$^{ns}$ | 80.1 ± 2.4$^{ns}$ |
| Low-dose PDT ($\mu$g/mL BPD + 10 J/cm$^2$ light ($\lambda$ = 690 nm) | | | |
| 1.0 $\mu$g/mL BPD | 73.8 ± 8.0 | 49.7 ± 2.0$^b$ | 28.0 ± 4.9$^c$ |
| 0.25 $\mu$g/mL BPD | 79.7 ± 6.8 | 82.9 ± 4.1$^{ns}$ | 78.8 ± 1.7$^{ns}$ |

$^a$The viability of LC was determined via trypan blue or propidium iodide exclusion. Viabilities were evaluated with freshly isolated LC or LC that had been maintained in complete culture medium (RPMI-1640) supplemented with 10% FBS, 20 ng/mL M-CSF and GM-CSF for 24 hours (short-term) or 7 days (long-term) at 37° C. Data is expressed as mean ± standard deviation for three independent experiments using ten mice for each experiment.
$^b$p <0.001 by Student's t-test relative to the fresh isolates.
$^c$p <0.0001 by Student's t-test relative to the fresh isolates.
$^{ns}$Not significantly different (p >0.05 by Student's t-test) from the fresh isolates.

It was found that the low-dose PDT-induced decrease in the LC surface antigens after the short-term in vitro culture was similar to those obtained when analysis was performed within the first 6 hours post pre-treatment and isolation. Furthermore, it was found that low-dose PDT at a BPD dose of 0.25 $\mu$g/mL did not affect the viabilities of cells after short- and long-term culture (See Table 3). On the contrary, low-dose PDT at a BPD dose of 1.0 $\mu$g/mL significantly decreased the viability of LC after short- and long-term in vitro culture (Table 3). These data suggest that low-dose PDT, at a dose of BPD (1.0 μg/mL) and light, which modulates surface antigens of LC, was ultimately cytotoxic for LC. In contrast, the lower dose of BPD (0.25 μg/mL) and light (which was more effective in allograft extension) was not cytotoxic.

EXAMPLE 10

Effect of Low-dose PDT on the
LC ATPase Activity

The intense formalin-resistant ATPase staining displayed on the cell membrane of LC has been used extensively and reliably as a histochemical marker for these cells both in situ and in suspension (Girolomoni et al., *J Invest. Dermatol.*, 100:282 (1993). It was found that enriched LC, but not keratinocyte (KC) cell line (PAM 212), stained positive for ATPase, confirming that ATPase activity is restricted to the epidermal LC. The intensities of ATPase staining on epidermal cells from untreated donor skin were similar to those observed on the epidermal cells from donor skin treated with low-dose PDT at a BPD dose of 0.25 μg/mL and light. In certain instances, the intensities of ATPase in this group appeared to be slightly greater than those of control donor skins. Unexpectedly, however, low-dose PDT at a higher dose of BPD (1.0 μg/mL of BPD) and light led to a 90% reduction in ATPase activity in comparison to the untreated controls.

It is possible that the stripping of the ecto-ATPase on LC could induce cell death. Interestingly, it has been suggested that the enzyme provides protection against extracellular ATP-induced permeabilization (Girolomoni, et al,. *J. Invest. Dermatol.*, 100:282 (1993)) and the subsequent induction of apoptosis upon exposure to extracellular ATP (Zanovello et al., *J. Immunol.* 145:1545 (1990)). Without being limited to such a theory, it appears that the mechanism of the low-dose PDT-induced prolongation of skin allograft survival depends on the dose of BPD: cytotoxicity of LC at the relatively higher dose of BPD (1.0 μg/mL), and the modulation of LC surface antigens at the lower (optimal) dose of BPD (0.25 μg/mL) and light. Because optimal skin graft prolongation was observed at a dose of BPD (0.25 μg/mL) and light, where there was no obvious toxicity of LC in culture, it is hypothesized that total depletion of donor-derived dendritic cells may not be the best way to achieve the much desired donor-specific tolerance in cell, tissue or organ transplantation. However, unless otherwise stated, it is not intended that the invention be in any way limited by this hypothesis.

EXAMPLE 11

Effect of Transdermal PDT on LC Migration.

Extensive studies by Kripke and colleagues (Kripke et al., *J. Immunol.*, 145:2833–38 (1990)) on the induction of contact hypersensitivity (CHS) to a fluorescent contact allergen, fluorescein isothiocyanate (FITC), have provided a useful model for studying the fate and activity of epidermal LC. These studies have shown that, after the topical application of the fluorescent contact allergen, the FITC-bearing LC migrated out of the skin and collected in the local draining lymph nodes, where they interacted with T cells to initiate a CHS.

Using an in vivo model in which BPD was activated in mice by irradiating the whole body with light at a wavelength of 690 nm ("transdermal PDT"), the effect of PDT on the migration of LC was evaluated in response to the topical application of a contact allergen, 8-chloromethyl-4,4-difluoro-1,3,5,7-tetramethyl-4-bora-3a,4a-diaza-indacene (Cell Tracker™ Green BODIPY®, Molecular Probe Inc., Eugene OR). Twenty-four hours following treatment and the application of the Green BODIPY®, draining lymph node cells were analyzed for allergen-bearing cells. Using a Coulter XL® flow cytometer, the fluorescence intensity of the draining lymph node cells from treated or untreated mice was assessed. Alternatively, the number of total viable cells were obtained from the superficial inguinal and axillary lymph nodes of these mice. The results obtained from mice given transdermal PDT and Green BODIPY® were compared with results from (1) mice that received only Green BODIPY® without transdermal PDT (positive control) or (2) the unmanipulated litter mates (naive or negative control).

The data suggested that transdermal PDT generally did not affect the migration of epidermal LC to the local draining lymph nodes. The contact sensitizer induced the migration of BODIPY-bearing epidermal cells (possibly LC) from the epidermis to the local draining lymph nodes. The mean intensities of the allergen-bearing cells from mice painted with the Green BODIPY® alone (positive control) were significantly (p<0.001 by the regular ANOVA) greater than the background fluorescence intensity obtained from naive mice that had received no contact allergen (negative control). On the contrary, transdermal PDT at the doses of BPD used (0.25 or 1.0 mg/kg) and light used (15 J/cm$^2$; λ=690±10 nm) had no significant effect on the migration of the Green BODIPY®-bearing epidermal cells to the draining lymph nodes.

Furthermore, we found that the contact allergen induced a moderate cellular increase (p<0.05 by the ANOVA) in the lymph nodes from an average value of 1.39×10$^7$ viable cells/mouse (negative control group) to an average value of 2.04×10$^7$ viable cells/mouse (positive control group). However, the cellularity (viable lymph node cells) of the lymph nodes from the positive control group was not significantly different (p>0.05 by the regular ANOVA and the Bonferroni multiple comparison test) from those of the treated groups receiving antigen.

EXAMPLE 12

Effect of Transdermal PDT on Infiltration of
Inflammatory Cells into Grafts During Skin
Allograft Rejection.

Several types of host cells typically infiltrate an allograft during rejection. Most of the infiltrating cells (mainly mononuclear leukocytes) are equipped with receptors specific for the alloantigens on the graft. These cellular infiltrates are responsible for mediating the rejection process. The following experiments evaluated the effect of "low-dose PDT" on the development of histologic and immunohistologic changes consistent with skin allograft rejection.

Balb/c mice were engrafted with untreated donor skins (C57BL/6) or with donor skins pre-treated with "low-dose PDT" at the optimal dose of BPD (0.25 μg/mL) and light (10 J/cm$^2$). After sacrificing the animals, graft tissues were dissected at various times (4–8 days) post grafting. The pre-treated skin tissues were compared to the untreated control samples at matched time points post-transplantation.

For immunohistology, skin tissues were snap frozen in liquid nitrogen-chilled isopentane. The frozen tissue sections were immunostained with an alkaline-phosphatase streptavidin-biotin method, as described elsewhere (Ratkay et al., *Clin. Exp. Immunol.*, 98:52–59 (1994)), applying commercially available biotinylated monoclonal antibodies directed against the following mouse cell-surface antigens: MHC class II (I-A$^d$) and ICAM-1 antigens (LC, macrophages), CD4 (T helper) and CD8 (T cytotoxic). The immunostained slides were later evaluated "blind" using a light microscope. Scores were assigned reflecting the intensity of each stain using set scoring criteria, as follows: 0=absent of stain; 1=minimal stain at some areas; 2=mild stain; 3=mild to moderate areas of stain; 4=moderate areas of stain; 5=moderate to marked areas of stain; and 6=areas of marked staining intensity.

In addition, untreated or pre-treated graft tissues were fixed in 10% formalin, and sections were stained with haematoxylin and eosin, following which microscopic assessment of the H/E stained skin tissues were performed in a "double blind" protocol. Scores were assigned to various anatomic/pathologic changes that reflected the degree of inflammation and vascular change using the following set criteria: 0=absent of inflammatory infiltrates; 1=minimal infiltrating cells; 2=mild infiltration; 3=mild to moderate infiltration; 4=moderate infiltration; 5=moderate to marked infiltration; and 6=marked infiltration.

Our immunohistological and histological results showed that "low-dose PDT" kept the level of the cellular infiltration into the graft at a low level as compared with the control grafts. In contrast to the control group, the speed of cellular infiltration, which is a prelude to graft rejection, was less intense in the "low-dose PDT"-treated grafts. This was evident histologically in the infiltration of the inflammatory cells into the grafts and immunohistologically in the intensities of staining for CD8, MHC class II and ICAM-1 surface antigens. A general overview of all the skin samples assessed showed that the treated samples usually had smaller focal infiltrates staining for ICAM-1 and MHC class II at the basal dermis of the graft than the control samples. The infiltrates were significantly lower in CD8-staining cells and low or negative for CD4-staining cells in the treated groups, as compared with the control skin sections. Histologically, "low-dose PDT" induced a delay in the onset and a decrease in intensity of the inflammatory cell infiltrate. Furthermore, there was a significant decrease in the extent of hemorrhage in the grafts of the treated. Edema was slightly less or similar at all days in both the treated and control groups. Still further, the onset of cutaneous muscle degeneration was delayed, and the degree of degeneration was less in the treated samples than in the control samples. Mineralization of the muscle fibers was occasionally present in some of the animals that received "low-dose PDT"-treated donor skins.

In skin allografts, Langerhans cells (LC) are known to initiate graft rejection in the draining lymph nodes of graft recipients by presenting their antigens to both CD4$^+$ and CD8$^+$ T cells. These alloantigen-specific T cells subsequently migrate to the graft to mediate the rejection process. On the basis of our previous findings, which suggested that "low-dose PDT" down-modulates the antigen-presenting functions of LC, it appears that the lower levels of inflammatory cellular infiltrates that migrate into a graft might be a consequence of the inefficient allostimulatory functions of LC. However, the present invention is not to be bound in any way by this theory, unless clearly stated to the contrary.

EXAMPLE 13

Modification of the Immunostimulatory Properties of Murine Splenic Dendritic Cells by Photosensitization with Benzoporphyrin Derivative (BPD, Verteporfin) and Visible Light Since dendritic cells ("DC") have been thought to propagate primary immune responses, an experiment was performed to determine whether BPD, with or without light, might modify the immunostimulatory behavior of DC in the mixed leukocyte reaction ("MLR") or the expression levels of different immunoregulatory molecules. When studied by flow cytometry, it was found that treatment of DBA/2 mouse splenic DC (greater than 85% purity) with light (5 Joules/cm$^2$) alone or BPD($\leq$2 $\mu$g/ml) alone did not alter the cells' ability to stimulate the proliferation of allogeneic T cells in a MLR. Further, their expression (mean channel fluorescence) for MHC Class I, MHC Class II, ICAM-1, CD80, CD86, LFA-1 (CD11a), Mac-1 (CD11b), CD18 antigens, or the CD-specific marker NLDC-145, was not significantly altered.

However, treatment of DC with 15 ng/ml BPD and light virtually eliminated (greater than 85%) their capacity to stimulate the MLR. Furthermore, DC surface levels of MHC Class I, MHC Class II, ICAM-1, CD80, and CD86 fell to 40–65% of control levels within 24 hours after the photodynamic treatment. In contrast, levels of CD11b were unaffected by this treatment, while the relative expression of LFA-1 and NLDC-145 was enhanced.

Cell integrity was verified by propidium iodide and Trypan blue staining. It was subsequently shown that the decrease in MHC Class I and ICAM-1 expression on DC produced by BPD and light was detectable within one hour, was maximal after four hours, and persisted for a minimum of 48 hours. The rapid synchronous nature of receptor down-regulation by DC suggests that the photodynamic treatment of these cells may have de-arranged the cytoskeleton, which may represent a cellular mechanism by which BPD and visible light interfere with immune reactivity.

It will be clear to those skilled in the art that modifications and/or variations of the disclosed subject matter can be made without departing from the scope of the invention claimed below.

We claim:

1. A method for modifying donor tissue so as to reduce the rejection of allografts comprising said donor tissue which unmodified donor tissue contains antigen presenting cells (APCs), which method comprises:

exposing said donor tissue which has been treated with a photosensitizing agent having an absorption maximum between 400–900 nm, to light having a wavelength absorbed by said photosensitizing agent for a time sufficient to diminish immunogenicity by functionally attenuating the APCs in the donor tissue under conditions wherein said light is not cytotoxic to said APCs.

2. A method according to claim 1, wherein the donor tissue is skin tissue or pancreatic islets.

3. A method according to claim 1, wherein said photosensitizing agent is a green porphyrin.

4. A method according to claim 1, wherein said treatment with said photosensitizing agent comprises contacting said tissue with a solution of said photosensitizing agent in a concentration of about 0.25 µg/ml.

5. A method according to claim 1 wherein said modified donor tissue is suspended in an electrolyte solution during said exposing to light.

6. A method according to claim 1, wherein the dose of said light during said exposing is about 10 J/cm$^2$.

7. A donor tissue having a reduced susceptibility of allograft rejection, prepared by a method which comprises exposing said donor tissue which has been treated with a photosensitizing agent having an absorption maximum between 400–900 mn, to light having a wavelength absorbed by said photosensitizing agent for a time sufficient to diminish immunogenicity by functionally attenuating the APCs in the donor tissue under conditions wherein said light is not cytotoxic to said APCs.

* * * * *